United States Patent [19]
Bockowski et al.

[11] Patent Number: 5,866,614
[45] Date of Patent: Feb. 2, 1999

[54] METHODS FOR FUMIGATING SOIL USING ACROLEIN

[75] Inventors: Edmund J. Bockowski, Chalfont; Dwight P. Davis, Holland, both of Pa.

[73] Assignee: BetzDearborn Inc., Trevose, Pa.

[21] Appl. No.: 906,891

[22] Filed: Aug. 6, 1997

[51] Int. Cl.$^6$ ..................................................... A01N 35/00
[52] U.S. Cl. .......................... 514/693; 504/161; 111/900
[58] Field of Search ........................... 504/161; 514/693; 111/900

[56] References Cited

U.S. PATENT DOCUMENTS

| | | | |
|---|---|---|---|
| 2,959,476 | 11/1960 | Van Overbeek | 71/2.7 |
| 3,028,304 | 4/1962 | Kreutzer | 514/703 |
| 3,250,667 | 5/1966 | Legator | 162/190 |
| 3,298,906 | 1/1967 | Knowles et al. | 167/22 |
| 3,380,462 | 4/1968 | Schieber et al. | 137/3 |
| 3,690,857 | 9/1972 | Blair, Jr. | 71/66 |
| 4,851,583 | 7/1989 | Bockowski et al. | 568/465 |
| 5,079,266 | 1/1992 | Bockowski et al. | 514/703 |
| 5,081,314 | 1/1992 | Kissel et al. | 568/479 |
| 5,171,454 | 12/1992 | Bockowski et al. | 210/764 |
| 5,243,082 | 9/1993 | Etzkorn et al. | 568/465 |
| 5,500,220 | 3/1996 | Roe et al. | 424/410 |

OTHER PUBLICATIONS

McKenry et al., "First–year evaluation of tree and vine growth and nematode development following 17 pre–plant treatments", !(% Annual International Research Conference on Methyl Bromide Alternatives and Emissions Reductions, p. 37/1–37/2. Meeting held on.

Soil Disinfestation, Ed. D. Mulder, Elsvier Scientific Publishing Corp., 1979,pp. 9–15 and 53–121

The Merck Index, Twelfth Edition, 1996, p. 23.

"Evaluation of Some Nonhalogenated compounds as Fumigants Against Larvae of the Caribbean Fruit Fly," J. F. Carroll et al., Journal of Economic Entomology, Feb. 1982, pp. 137–140.

"Chemical Control of Mussel Settlement in a Cooling Water System Using Acrolein," J. W. Rustenbil et al., Environmental Pollution (Series 4) 25 (1981), pp. 187–195.

"Bisulfate Adducts of Acrolein," H D. Finch, J. Org. Chem., 27, 649–651, Feb. 1962.

"Solid Sorbent for Sampling Acrolein in Air," A. Gold et al., Analytical Chemistry, vol. 50, No. 13, Nov. 1978.

EPA Test Method, Acrolein and Acrylonitrile—Method 603, Jul. 1982.

"Environmental and metabolid Fate of Acrolein in Water, Aquatic Sediment, Fish and Shellfish," M. Kovacs et al., Society of Environmental Toxicology and Chemistry, Annual Meeting, Nov. 14–18m 1993.

"Metabolic Fate of Acrolein in Plants and Livestock," Society of Environmental Toxicology and Chemistry, Annual Meeting, Nov. 14–18, 1993.

"The Berry and the Poison," J. Wheelwright, Smithsonian, Dec. 1996, pp. 40–51.

*Primary Examiner*—Sandra E. Saucier
*Assistant Examiner*—Vera Afremova
*Attorney, Agent, or Firm*—Alexander D. Ricci; Philip H. Von Neida

[57] ABSTRACT

The present invention provides for methods for fumigating soil containing deleterious organisms such as nematodes. The methods utilize an effective amount of acrolein which when added to the soil will control the organisms but will not exhibit phytotoxicity towards the existing or future plant life and an effective amount of a detoxification compound such as for example: sulfites, bisulfites, ammonia or ammonium compounds.

5 Claims, No Drawings

METHODS FOR FUMIGATING SOIL USING ACROLEIN

FIELD OF THE INVENTION

The present invention relates to methods for fumigating soil to control deleterious organisms. More particularly, the present invention provides for the use of acrolein to control deleterious organisms in soil while minimizing or eliminating the phytotoxic effects.

BACKGROUND OF THE INVENTION

Fungi, bacteria, nematodes, viruses and insects can cause problems in soil designated for growing. This soil contamination will lead to the dying off of plants, growth rate problems, root problems and production decrease. The need for soil disinfestation is thus recognized as a manifest one.

Various disinfestation methods exist. Sterilization at greater than 100° C. is a total biocide treatment. Pasteurization at 70° C. will eliminate many pathogenic fungi and their specific survival forms.

Chemical treatments can be divided into two classes: total disinfectants and limited biocide or biostatic activity. Examples of total disinfectants which are used with higher financial risks involved include chloropicrin, methyl bromide and methylisocyanate. Limited activity biocides include dichloroprene.

Methyl bromide is an odorless gas which is delivered to soils with or without the use of a plastic tarpaulin. Methyl bromide is a primary fumigant for controlling nematodes, weeds and fungi primarily for tomatoes, ornamentals, tobacco, peppers, strawberries and forest seedlings. One advantage of methyl bromide as a fumigant is that it evaporates; however, at 50 gram/$m^2$ methyl bromide leaves 10 to 20 ppm of bromide or bromine compounds as a residue in the soil.

However, due to the United States' participation in the Montreal Protocol, compounds that have a detrimental effect on the ozone layer will be banned as of Jan. 1, 2001. These compounds include chlorinated fluorocarbons (CFC's) and methyl bromide. The 150 countries party to the United National Montreal Protocol are acting globally on what is pledged to be a complete phase out of methyl bromide and CFC's.

The economic effects of this ban in the United States and particularly California and Florida are manifest. The economic losses to these two states may be profound and total $900 million if a new approved fumigant cannot be found in time to replace the methyl bromide.

To that end, an alternative fumigant that possesses attributes similar to methyl bromide (no toxic residue, efficacy, and ease of use/economics) must be found. This fumigant should leave no toxic soil residue, should be biodegradable, and should exhibit efficacy against a wide variety of soil pathogens, as well as insects and nematodes.

The present inventors have discovered means for employing acrolein as a soil fumigant. Acrolein is a known pesticide that is used to treat liquids containing slime-forming microorganisms. Acrolein has been found to effectively control bacteria such as *Bacillus subtilis*. *Pseudomonas putrefaciens* and *Escherichia coli*; fungi such as *Penicillium italicum*, *Saccharomyces cereviseae* and *Helminthosporium turcicum*; algae; macroinvertebrates, such as snails and clams; and aquatic plants and weeds. Acrolein is also more effective than other biocides, such as chlorine, in controlling macroinvertebrates and submerged, as well as floating, aquatic weeds and algae.

From an environmental point of view, acrolein is a good biocide because it is effective, detoxified readily and inexpensively, and is non-persistent. Water solutions of acrolein are readily and conveniently neutralized for disposal with sodium bisulfite. This reaction produces a non-toxic water-soluble salt. Acrolein is also neutralized by reacting with materials present in natural waters and is therefore self-neutralizing. Also, one major advantage over methyl bromide is that there is no residue left in the soil other than normal carbohydrate residuals, that can be readily assimilated by plants and other organisms.

The present inventors have also discovered that acrolein can be administered to soil as a fumigant while avoiding the usual effects of phytotoxicity, which would otherwise prevent its utilization, by the specific method of application.

U.S. Pat. No. 2,959,476 discloses a method of controlling aquatic life in aqueous systems. This method is directed particularly to aquatic weeds and comprises adding a toxic quantity of acrolein to the particular body of water.

U.S. Pat. No. 3,250,667 discloses a method of controlling microorganisms encountered in the manufacture of paper. This method employs acrolein to inhibit the formation of slime-forming and corrosion-promoting microorganisms in the aqueous system of a paper-manufacturing plant. Fungi and bacteria are the primary organisms responsible for slimes in papermaking aqueous systems.

U.S. Pat. No. 3,298,906 discloses the use of acrolein acetals to protect a variety of plants from plant parasitic nematodes. This patent also discloses that the acrolein acetals can be combined with other known fungicides to control a broader spectrum of fungi.

U.S. Pat. No. 3,380,462 discloses a special system to utilize acrolein in a safe manner. This apparatus provides for creating a controlled pressure zone in the liquid to be treated and adding the acrolein to that zone.

U.S. Pat. No. 3,690,857 discloses the use of acrolein diacetals in watery media to kill aquatic weeds and other undesired life forms. This method will control the growth of these aquatic organisms while avoiding killing the majority of the fish present.

DETAILED DESCRIPTION OF THE INVENTION

The present invention provides for methods for fumigating soil containing deleterious organisms while controlling phytotoxicity comprising adding to the soil an effective amount for the purpose of acrolein.

For purposes of the present invention, the term "an effective amount for the purpose" is defined as the amount of acrolein which when added to the soil will control the deleterious organisms, yet will not exhibit phytotoxicity to the plants, because of the specific methods and timing of the addition.

Typical soils that can be treated by the methods of the present invention are those capable of growing a food or an ornamental crop such as strawberries, almonds, grapes, ornamental flowers, tobacco, tomatoes, watermelon, grass sod, apples, peanuts, lettuce, soybeans, onions, peaches, sugar cane, wheat, cherries, and other field crops and ornamental species.

The deleterious organisms treated by the methods of the present invention include viruses, bacteria, fungi, insects, and nematodes. The methods of the present invention will also be effective against other pathogens typically found in soils.

Applicants are able to achieve control of deleterious organisms by killing them while exhibiting no phytotoxicity to the plants already present or waiting to be planted. This effect is achieved not only by the amount of acrolein that is added to the soil, but in the manner in which it is added. This manner is important as acrolein is a known phytotoxic compound, and this manner of addition will assure cidal effects controlling phytotoxicity.

Acrolein may be applied to the site by a number of known means. For example, acrolein may be supplied in cylinders or concentrated solutions such as could be made available from current acrolein manufacturers such as Degussa Corp.

Another delivery means is by the on-site, thermal decomposition of acrolein dimer (3,4-dihydro-2H-pyran-2-carboxaldehyde or 2-formyl-3,4-dihydro-2H-pyran). This can generally be accomplished by heating the acrolein dimer at 400° C. at ambient pressure in a simple packed heat exchange tube. Acrolein dimer is available from Union Carbide Corp. as Prosan® 1100.

A third means of generating acrolein is through the dehydration of glycerol by the reaction:

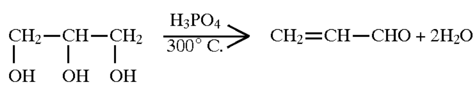

This method is relatively inexpensive as glycerol and phosphoric acid are inexpensive. However, there is a disadvantage regarding the generation of an acid waste which must be either treated or disposed of.

Another means for producing acrolein is by oxidation of propylene. This oxidation occurs with specialized catalysts at 450° to 500° C. This reaction is more fully described in U.S. Pat. No. 5,081,314, the contents of which are wholly incorporated by reference herein.

Another method for producing acrolein is demonstrated in U.S. Pat. No. 5,079,266. This reference teaches the catalytic hydrolysis of an acrolein acetal to produce acrolein. The '266 patent, the contents of which are wholly incorporated by reference herein, teaches one of the safer means to produce acrolein.

As can be seen, there are a number of ways to generate acrolein. Any one of them can be employed to generate the acrolein used in the methods of the present invention. They differ by cost, safety and ease of production.

The acrolein can be applied to the soil containing the deleterious organisms by a number of methods. The acrolein can be sprayed onto or injected into the soil. Proper soil cultivation prior to application is necessary as is true of other fumigants.

For purposes of the present invention, the soil is dosed with acrolein to establish the demand present. Once the demand is analyzed and established, a dosage rate from about 1 to about 100 grams/$M^2$ above demand is recommended, with a dosage rate of about 5 to about 50 grams/$M^2$ more preferred. Analysis of the soil pest population by conventional methods will permit optimization of treatment levels.

Typical devices for applying chemicals to the soil include a gravity flow applicator which is common for treatment of rows or smaller area. This type of injector can be of the chisel, tooth or shank type. Plough applications can also be employed particularly on light soils.

Blade applicators are employed to provide an even distribution of the chemicals at the depth of application. Following application, of course, the soil must be sealed in a fashion so that the acrolein does not leak out as a gas. The sealing methods can be as simple as rolling over the soil to covering with plastic for the length of time necessary for the chemicals to act.

The acrolein employed in the methods of the present invention may be added to the soil in any convenient medium that is compatible with both the acrolein and the soil to be treated. One method would use acrolein in a solvent medium. Preferably this solvent is water, which when utilized will aid in soil penetration. The acrolein may also be added contained in a polymer or gel where contact with water present in the soil will allow for the polymer or gel to dissolve and allow introduction of the acrolein into the soil.

Other methods of delivery useful in the method of the present invention include microencapsulation or controlled release. Acrolein may be trapped in Linde 13X molecular sieves (activated). Approximately 20 to 25% acrolein may be trapped on a weight basis. The trapped acrolein is stable under typical conditions but is released quickly in the presence of moisture.

Diallylidene pentaerythritol (DAP) is an acrolein acetal in solid form which can be mixed with a solid acid such as sodium acid sulfate or strong sulfonic acid resin and a small amount of high molecular weight sodium carboxymethyl cellulose. For example, 50% DAP, 49% $NaHSO_4$, and 1% Hercules CMC HT in the presence of moisture will release acrolein to the soil. The rate of release will depend upon the amount of water present.

One means to control the phytotoxic effects of the acrolein within the purview of the present invention is through the detoxification of acrolein. By detoxifying acrolein, it is possible to allow the acrolein to control any or all of the deleterious organisms and yet render it incapable of phytotoxicity.

In "Environmental and Metabolic Fate of Acrolein in Water, Aquatic Sediment, Fish and Shellfish", Kovacs et al., the authors discuss the results of testing that demonstrate that acrolein does not persist in the aquatic environment or aquatic species.

In "Metabolic Fate of Acrolein in Plants and Livestock", Loftus et al., the studies address metabolism of acrolein in plants and animals and determine that acrolein does not persist in plants or animals.

The natural and chemical decay of acrolein will vary with pH, temperature, and other soil conditions. In the presence of certain bacteria and chemicals, acrolein will be biodegraded and/or converted to various carbohydrate compounds, as needed by the organism.

A more controlled method of detoxification is by sulfite detoxification. Acrolein may be detoxified with sulfites and bisulfites by the following reactions:

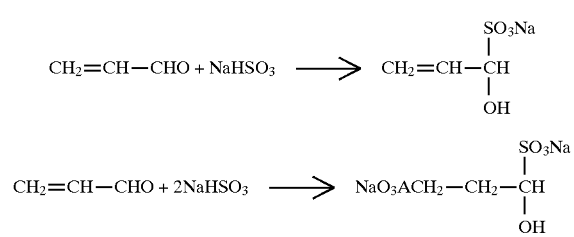

These reactions are fairly rapid and represent an environmentally significant feature of acrolein. Two moles of sulfite are required at a minimum for each mole of excess acrolein requiring detoxification. An ammonium bisulfite salt or sulfite salt solution is preferred.

Another means to detoxify acrolein is with ammonia or ammonium compounds. The reaction products of acrolein and ammonia, include propenediamine, and other hydroxylated $C_3$ amines, all of which will be biodegraded and assimilated by plants and other soil organisms. One advantage of this method is that acrolein will react with ammonia or ammonium nitrate derived from fertilizer which may be present in or may be added to the soil. Acrolein residues can be destroyed, as such, within hours. To that end, various analytical tests have been developed to test for acrolein (EPA Test Method 603 and NIOSH P and CAM 211) which can be utilized in conjunction with the detoxification methods.

Acrolein has been tested and has demonstrated its properties as a general biocide. Acrolein's effectiveness against mussels is discussed in "Chemical Control of Mussel Settlement in a Cooling Water System Using Acrolein", Rustenbil et al., Environ. Pollut. Ser. A., 25 (1981), 187, 195. Its effectiveness against *Thiobaccilus ferroxidans* has been demonstrated in U.S. Pat. No. 5,171,454.

U.S. Pat. No. 5,500,220 demonstrates the effectiveness of acrolein against the adult confused flour beetle, *Tribolium confusum* Jaquelin du Val; adult cigarette beetle, *Lasioderma serricorne*; larvae of black carpet beetles, *Attegenus unicolor*; and all life stages of the rice weevil, *Sitophilus orvzae*.

"Evaluation of Some Nonhalogenated Compounds as Fumigants Against Larvae of a Caribbean Fruit Fly", Carroll et al., "Journal of Economic Entomology", February 1982, 137 discusses the effectiveness of acrolein against *Anastrepha suspensa*.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A method for controlling deleterious organisms in soil comprising the steps of:
   a) adding to said soil an effective amount of acrolein in order to control deleterious organisms; and
   b) adding to said soil an effective amount of a compound to detoxify the acrolein.

2. The method as claimed in claim 1 wherein from about 1 grams to about 100 grams of acrolein are added per square meter of soil above demand.

3. The method as claimed in claim 1 wherein said detoxification compound is selected from the group consisting of sulfites, bisulfites, ammonia and ammonium compounds.

4. The method as claimed in claim 3 wherein said detoxification compound is ammonium bisulfite salt or sulfite salt.

5. A method for fumigating soil containing deleterious organisms comprising the steps of:
   a) analyzing said soil to establish demand for acrolein;
   b) adding an effective amount over demand for the purpose of said acrolein to said soil;
   c) detoxifying said soil by adding to said soil a detoxifying agent selected from the group consisting of ammonia, ammonium compounds, sulfites and bisulfites.

* * * * *